(12) United States Patent
Kriveshko et al.

(10) Patent No.: US 9,937,022 B2
(45) Date of Patent: Apr. 10, 2018

(54) NAVIGATING AMONG IMAGES OF AN OBJECT IN 3D SPACE

(75) Inventors: Ilya A. Kriveshko, Littleton, MA (US); Dmitriy A. Dedkov, Everett, MA (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 1009 days.

(21) Appl. No.: 12/811,268

(22) PCT Filed: Jan. 4, 2009

(86) PCT No.: PCT/US2009/030064
§ 371 (c)(1),
(2), (4) Date: Jun. 30, 2010

(87) PCT Pub. No.: WO2009/089125
PCT Pub. Date: Jul. 16, 2009

(65) Prior Publication Data
US 2010/0283781 A1    Nov. 11, 2010

Related U.S. Application Data

(60) Provisional application No. 61/019,159, filed on Jan. 4, 2008.

(51) Int. Cl.
*G06T 13/20* (2011.01)
*A61C 13/00* (2006.01)
(Continued)

(52) U.S. Cl.
CPC ...... *A61C 13/0004* (2013.01); *G06K 9/00201* (2013.01); *G06K 9/00214* (2013.01);
(Continued)

(58) Field of Classification Search
CPC ..... G06T 13/00; G06T 7/0012; G06T 19/003; G06T 2207/30004; G06T 2207/30036
See application file for complete search history.

(56) References Cited

U.S. PATENT DOCUMENTS 5,276,785 A * 1/1994 Mackinlay .......... G06F 3/04815
345/427
5,359,703 A * 10/1994 Robertson ........... G06F 3/04815
345/419
(Continued)

FOREIGN PATENT DOCUMENTS

KR    2007-0039641    4/2007

OTHER PUBLICATIONS

The Hybrid Display: Smooth Transition between Virtual and Real Views for Location Unbound Observations in Telepresence Applications, Leupold et al., 2005.*
(Continued)

*Primary Examiner* — Barry Drennan
*Assistant Examiner* — Phong Nguyen

(57) ABSTRACT

A three-dimensional model of an object is employed to aid in navigation among a number of images of the object taken from various viewpoints. In general, an image of an object such as a digital photograph is displayed in a user interface or the like. When a user selects a point within the display that corresponds to a location on the surface of the object, another image may be identified that provides a better view of the object. In order to maintain user orientation to the subject matter while navigating to this destination viewpoint, the display may switch to a model view and a fly-over to the destination viewpoint may be animated using the model. When the destination viewpoint is reached, the display may return to an image view for further inspection, marking, or other manipulation by the user.

22 Claims, 6 Drawing Sheets

(51) Int. Cl.
*G06K 9/00* (2006.01)
*G06T 17/00* (2006.01)
*H04N 13/02* (2006.01)

(52) U.S. Cl.
CPC ......... *G06T 17/00* (2013.01); *H04N 13/0221* (2013.01); *G06T 2207/10012* (2013.01); *G06T 2210/41* (2013.01)

(56) References Cited

U.S. PATENT DOCUMENTS

| | | | |
|---|---|---|---|
| 5,850,352 A * | 12/1998 | Moezzi | G06T 15/10 345/419 |
| 6,208,347 B1 * | 3/2001 | Migdal | G06T 17/20 345/419 |
| 6,219,437 B1 | 4/2001 | Baldur | |
| 6,272,235 B1 * | 8/2001 | Bacus | G01N 15/1475 382/133 |
| 6,477,268 B1 * | 11/2002 | Chiang | F04B 49/035 382/154 |
| 6,525,732 B1 * | 2/2003 | Gadh | G06T 15/20 345/428 |
| 6,614,452 B1 * | 9/2003 | Cable | A61B 5/0059 382/280 |
| 6,973,204 B2 | 12/2005 | Adachi | |
| 7,046,840 B2 * | 5/2006 | Chang | G06T 17/10 345/420 |
| 7,085,323 B2 | 8/2006 | Hong | |
| 7,372,642 B2 * | 5/2008 | Rohaly et al. | 359/740 |
| 7,508,430 B1 | 3/2009 | Oten et al. | |
| 7,605,817 B2 | 10/2009 | Zhang et al. | |
| 7,813,591 B2 | 10/2010 | Paley | |
| 8,228,994 B2 | 7/2012 | Wu | |
| 8,467,628 B2 | 6/2013 | Coffman | |
| 2001/0016063 A1 | 8/2001 | Albeck et al. | |
| 2001/0033326 A1 | 10/2001 | Goldstein et al. | |
| 2002/0135678 A1 * | 9/2002 | Bacus | G01N 1/312 348/143 |
| 2002/0136444 A1 | 9/2002 | Brown et al. | |
| 2002/0140698 A1 * | 10/2002 | Robertson | G06F 3/04815 345/427 |
| 2003/0013966 A1 * | 1/2003 | Barnes | A61B 5/0402 600/446 |
| 2003/0090654 A1 * | 5/2003 | Bazin | G06T 13/80 356/317 |
| 2003/0132936 A1 * | 7/2003 | Kreeger | G06T 7/0012 345/420 |
| 2004/0015327 A1 * | 1/2004 | Sachdeva | A61C 7/00 702/167 |
| 2004/0051783 A1 * | 3/2004 | Chellappa | H04N 13/026 348/46 |
| 2004/0085335 A1 * | 5/2004 | Burlnyk | G06F 3/04815 715/716 |
| 2004/0197728 A1 | 10/2004 | Abolfathi et al. | |
| 2004/0239699 A1 * | 12/2004 | Uyttendaele | G06F 17/30056 715/716 |
| 2005/0089213 A1 | 4/2005 | Geng | |
| 2005/0089214 A1 | 4/2005 | Rubbert et al. | |
| 2005/0089822 A1 | 4/2005 | Geng | |
| 2005/0151963 A1 * | 7/2005 | Pulla | G01B 21/04 356/139.03 |
| 2005/0182295 A1 * | 8/2005 | Soper et al. | 600/117 |
| 2005/0201612 A1 | 9/2005 | Park | |
| 2005/0285874 A1 | 12/2005 | Zitnick, II et al. | |
| 2006/0028474 A1 * | 2/2006 | Pfister | G06T 13/20 345/473 |
| 2006/0066612 A1 | 3/2006 | Yang | |
| 2006/0103678 A1 * | 5/2006 | Cathier | G06T 19/00 345/649 |
| 2006/0127852 A1 * | 6/2006 | Wen | A61C 7/00 433/213 |
| 2006/0132482 A1 * | 6/2006 | Oh | G06T 13/80 345/419 |
| 2006/0154198 A1 * | 7/2006 | Durbin | A61C 9/00 433/29 |
| 2006/0204076 A1 | 9/2006 | Avanish et al. | |
| 2006/0208927 A1 * | 9/2006 | Poor | G01C 21/00 340/995.1 |
| 2007/0030575 A1 * | 2/2007 | Yen | G02B 7/102 359/676 |
| 2007/0031064 A1 | 2/2007 | Zhao et al. | |
| 2007/0103460 A1 | 5/2007 | Zhang et al. | |
| 2007/0110338 A1 * | 5/2007 | Snavely | G06F 17/30274 382/305 |
| 2007/0127813 A1 | 6/2007 | Shah | |
| 2007/0141534 A1 | 6/2007 | Wen | |
| 2007/0172101 A1 | 7/2007 | Kriveshko et al. | |
| 2007/0188601 A1 * | 8/2007 | Rohaly | H04N 13/0217 348/47 |
| 2007/0253618 A1 | 11/2007 | Kim et al. | |
| 2008/0025646 A1 * | 1/2008 | Aguera y Arcas et al. | 382/305 |
| 2008/0238916 A1 * | 10/2008 | Ghosh et al. | 345/419 |
| 2009/0129630 A1 * | 5/2009 | Gloudemans et al. | 382/103 |
| 2009/0153549 A1 * | 6/2009 | Lynch et al. | 345/419 |
| 2009/0179895 A1 * | 7/2009 | Zhu | G06F 17/30241 345/424 |
| 2010/0135543 A1 * | 6/2010 | Weese et al. | 382/128 |

OTHER PUBLICATIONS

Debevec et al., Modeling and Rendering Architecture from Photographs: A hybrid Geometry- and Image-Based Approach, 1996, SIGGRAPH, pp. 11-20.*

Triggs et al., "Bundle adjustment-a modern synthesis" Vision algorithms: theory and practice (2000) pp. 153-177.

Dorst, "First Order Propagation of the Procrustes Method for 3D Attitude Estimation", IEEE Transactions on Pattern Analysis and Machine Intelligence, vol. 27, No. 2, Feb. 2005, pp. 221-229.

Zhang, "Hierarchical Block-Based Disparity Estimation Using Mean Absolute Difference and Dynamic Programming", Proc. Of the Int. Workshop on Very Low Bitrate Video Coding, pp. 114, 118, Athens Greece, Oct. 11-12, 2001.

Rohaly et al., U.S. Appl. No. 12/811,236, filed Sep. 22, 2010.
Rohaly et al., U.S. Appl. No. 12/811,237, filed Sep. 27, 2010.
Zhang et al., U.S. Appl. No. 12/811,239, filed Sep. 22, 2010.
Zang et al., U.S. Appl. No. 12/811,242, filed Jun. 30, 2010.

* cited by examiner

NAVIGATING AMONG IMAGES OF AN OBJECT IN 3D SPACE

CROSS-REFERENCE TO RELATED APPLICATIONS

This application is a national stage filing under 35 U.S.C. 371 of PCT/US 2009/030064, filed Jan. 4, 2009, which claims priority to U.S. Provisional Application No. 61/019, 159, filed Jan. 4, 2008, the disclosure of which is incorporated by reference in their entirety herein.

BACKGROUND

There are a variety of techniques for capturing three-dimensional surface data from an object. The resulting three-dimensional model may be used directly for many purposes; however, in certain applications there may be valuable visual information (such as color, texture, shading, etc.) in two-dimensional photographs of the object. Where a number of images of the object are available from a number of different viewpoints, a user may wish to navigate from one viewpoint to another viewpoint while working with the three-dimensional model.

Some general approaches to three-dimensional navigation include point-and-click interfaces that provide animated fly-overs to selected locations using a three-dimensional model with an overlay of satellite pictures (such as Google Earth). However, in a visual inspection or similar environment, the navigation problem may be further constrained because the available source images are captured from disparate, and sometimes widely disparate, viewpoints that may vary with three degrees of freedom in position and rotation. In this environment, it may not be sufficient to simply choose an arbitrary viewpoint in response to a user input. It may further be necessary to reconcile a user's input with a finite collection of actual source images to select an image from a camera position and camera angle that offers a satisfactory view of the selected subject matter.

There remains a need for improved techniques for navigating among a number of images of an object in three-dimensional space.

SUMMARY

A three-dimensional model of an object is employed to aid in navigation among a number of images of the object taken from various viewpoints. In general, an image of an object such as a digital photograph is displayed in a user interface or the like. When a user selects a point within the display that corresponds to a location on the surface of the object, another image may be identified that provides a better view of that location. In order to maintain user orientation to the subject matter while navigating to this destination viewpoint, the display may switch to a model view and animate a fly-over to the destination viewpoint using the model. When the destination viewpoint is reached, the display may return to an image view for further inspection, marking, or other manipulation by the user.

In one aspect, disclosed herein is a method of navigating among a number of images taken of an object including displaying a first image of an object, the first image selected from a number of images taken of the object, the first image showing a surface of the object from a first viewpoint; receiving a selection of a location on the surface of the object; selecting a second image of the object from the number of images taken of the object, the second image selected to provide an improved view of the location on the surface of the object from a second viewpoint; rendering an animation of a spatial transition from the first viewpoint to the second viewpoint using a three-dimensional model of the object; displaying the animation; and displaying the second image upon reaching the second viewpoint in the animation.

Receiving the selection of the location may include receiving the selection from within a graphical user interface. Receiving the selection may include at least one of a mouse input and a touch screen input. The three-dimensional model may include a texture map that is derived from at least one image of the number of images. Selecting the second image may include displaying a plurality of candidate images selected from the number of images taken of the object and receiving a user selection of one of the plurality of candidate images. The number of images may include a plurality of frames of video data that originate from a center channel of a video camera having one or more side channels that capture data used to generate the three-dimensional model. Selecting the second image may include selecting a one of the number of images having a viewpoint that is most substantially normal to the surface at the location. Selecting the second image may include selecting a one of the number of images having the location nearest to the center thereof. The object may include human dentition. The object may include at least one of teeth, gums, dentures, and braces. The object may include a prepared tooth surface.

In another aspect, a system disclosed herein may include a computer; a display operatively coupled to the computer; a user input device that receives a user selection, the user input device operatively coupled to the computer; and a computer-usable medium operatively coupled to the computer. The computer-usable medium may have stored within it computer-readable instructions for execution by the computer to perform a method comprising the steps of: displaying a first image of an object on the display, the first image selected from a number of images taken of the object, the first image showing a surface of the object from a first viewpoint; receiving a selection of a location on the surface of the object from the user input device; selecting a second image of the object from the number of images taken of the object, the second image selected to provide an improved view of the location on the surface of the object from a second viewpoint; rendering an animation of a spatial transition from the first viewpoint to the second viewpoint using a three-dimensional model of the object; displaying the animation on the display; and displaying the second image on the display upon reaching the second viewpoint in the animation.

The user input device may include one or more of a mouse and a touch screen. The system may include a three-dimensional camera having a left channel and a right channel that capture spatial information, the camera operatively coupled to the computer; and computer-readable instructions for execution by the computer to construct the three-dimensional model from the spatial information, the computer-readable instructions stored within the computer-usable medium. The computer-usable medium may include one or more of a computer chip, an optical disk, and a magnetic disk. The display may be a three-dimensional display such as an autostereoscopic display.

In another aspect, a graphical user interface disclosed herein for navigating among a number of images taken of an object includes an image display area that alternately displays: a first image of an object, the first image showing a surface of the object from a first viewpoint; an animation of a spatial transition from the first viewpoint to a second viewpoint that provides an improved view of a user-selected location on the surface of the object in the first image, the animation rendered from a three-dimensional model of the object; and a second image of the object, the second image showing the object from the second viewpoint.

The animation may include a texture-mapped animation. The first image and the second image may be selected from a plurality of frames of video data that originate from a center channel of a video camera having one or more side channels that capture data used to generate the three-dimensional model. The object may include human dentition. The object may include at least one of teeth, gums, dentures, and braces. The object may include a prepared tooth surface.

BRIEF DESCRIPTION OF THE FIGURES

The following detailed description of certain embodiments may be understood by reference to the following figures.

DETAILED DESCRIPTION

Figure 1:
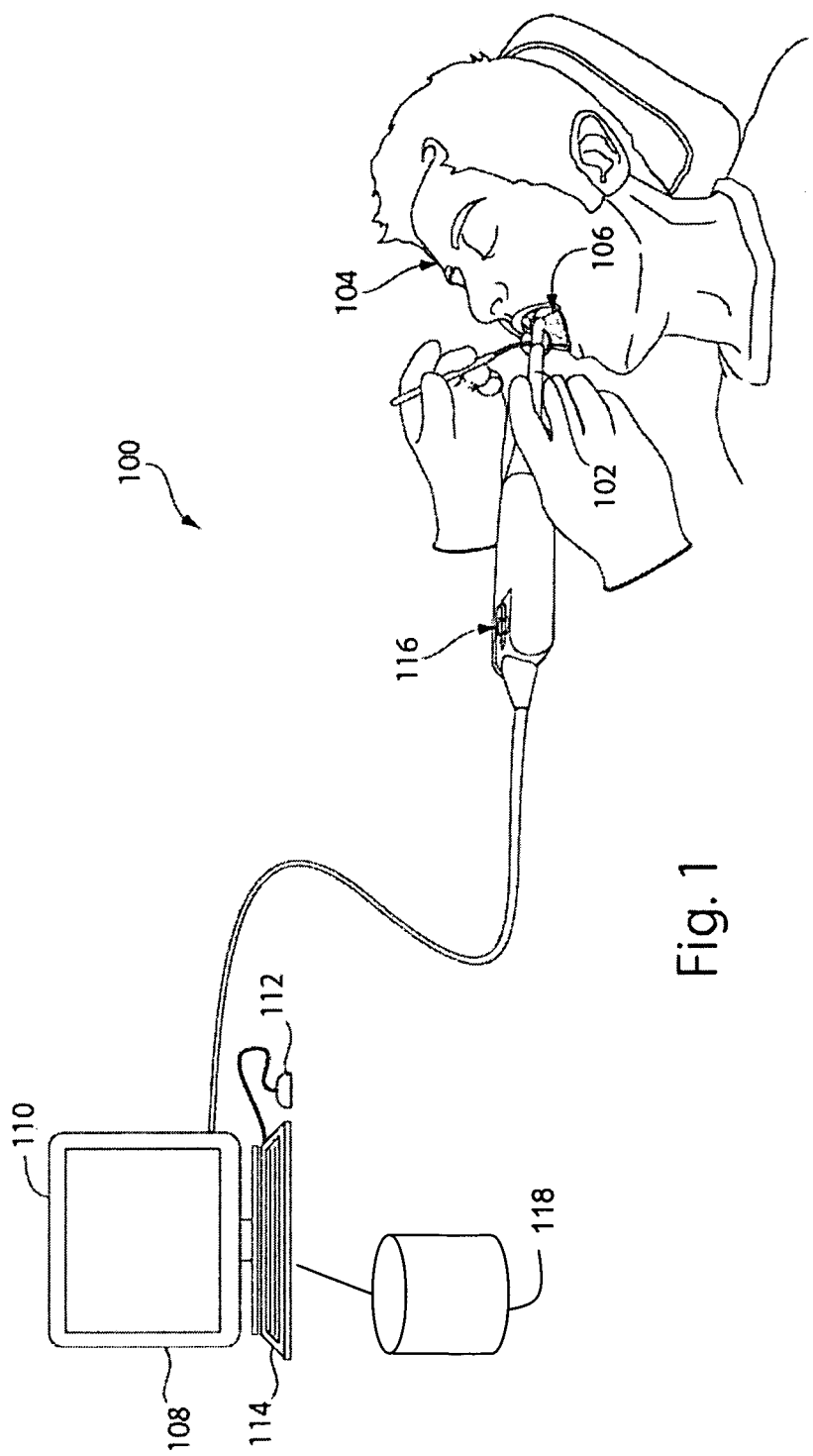
FIG. 1 depicts a three-dimensional scanning system.

In the following text, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

Disclosed herein are techniques for navigating among two-dimensional images of a three-dimensional object. The following description details specific scanning technologies and focuses on dental applications of three-dimensional imaging; however, it will be appreciated that variations, adaptations, and combinations of the methods and systems below will be apparent to one of ordinary skill in the art. For example, non-image based scanning techniques such as infrared time-of-flight techniques or structured light techniques using patterned projections may similarly be employed to capture three-dimensional data, and may be augmented with visible light digital video or still images that are captured substantially concurrently with three-dimensional measurements. Navigation among these video or still images may be enhanced using the techniques described herein. As another example, while digital dentistry is one useful application of the improved navigation systems of this disclosure, the techniques described herein may also be usefully employed to refine three-dimensional animation models acquired from scans of objects, or in a machine vision context to mark or evaluate scanned objects. All such variations, adaptations, and combinations are intended to fall within the scope of this disclosure.

In the following description, the term "image" generally refers to a two-dimensional set of pixels forming a two-dimensional view of a subject within an image plane. The term "image set" generally refers to a set of related two-dimensional images that might be resolved into three-dimensional data. The term "point cloud" generally refers to a three-dimensional set of points forming a three-dimensional view of the subject reconstructed from a number of two-dimensional images. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional model", "three-dimensional surface representation", "digital surface representation", "three-dimensional surface map", and the like, as used herein, are intended to refer to any three-dimensional reconstruction of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. In general, the three-dimensional model may be constructed out of a number of three-dimensional measurements from a three-dimensional camera. A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that a variety of three-dimensional rendering technologies exist, and may be usefully employed with the systems and methods disclosed herein. For example, the systems and methods described herein may usefully employ a holographic display, an autostereoscopic display, an anaglyph display, a head-mounted stereo display, or any other two-dimensional and/or three-dimensional display. As such, rendering as described herein should be interpreted broadly unless a narrower meaning is explicitly provided or otherwise clear from the context.

The term "dental object", as used herein, is intended to refer broadly to subject matter related to dentistry. This may include intraoral structures such as dentition, and more typically human dentition, such as individual teeth, quadrants, full arches, pairs of arches (which may be separate or in occlusion of various types), soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects such as the restorations, prostheses, appliances, hardware, and interim components of dental manufacture as described above.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

It will further be understood that terms such as "tool" or "control", when used to describe aspects of a user interface, are intended to refer generally to a variety of techniques that may be employed within a graphical user interface or other user interface to receive user input that stimulates or controls processing including without limitation drop-down lists, radio buttons, cursor and/or mouse actions (selections by point, selections by area, drag-and-drop operations, and so forth), check boxes, command lines, text input fields, messages and alerts, progress bars, and so forth. A tool or control may also include any physical hardware relating to the user input, such as a mouse, a keyboard, a display, a keypad, a track ball, and/or any other device that receives physical input from a user and converts the physical input into an input for use in a computerized system. Thus in the following description the terms "tool", "control" and the like should be broadly construed unless a more specific meaning is otherwise provided or clear from the context.

FIG. 1 depicts a three-dimensional scanning system that may be used with the systems and methods described herein. In general, the system 100 may include a camera 102 that captures images from a surface 106 of an object 104, such as a dental patient, and forwards the images to a computer 108, which may include a display 110 and one or more user-input devices 112, 114 such as a mouse 112 or a keyboard 114. The camera 102 may also include an integrated input or output device 116 such as a control input (e.g., button, touchpad, thumbwheel, etc.) or a display (e.g., LCD or LED display) to provide status information.

The camera 102 may include any camera or camera system suitable for capturing images from which a three-dimensional point cloud or other three-dimensional data may be recovered. For example, the camera 102 may employ a multi-aperture system as disclosed in U.S. Pat. No. 7,372,642 to Rohály et al., the entire content of which is incorporated herein by reference. While Rohály discloses one multi-aperture system, it will be appreciated that any multi-aperture system suitable for reconstructing a three-dimensional point cloud from a number of two-dimensional images may similarly be employed. In one multi-aperture embodiment, the camera 102 may include a plurality of apertures including a center aperture positioned along a center optical axis of a lens that provides a center channel for the camera 102, along with any associated imaging hardware. In such embodiments, the center channel may provide a conventional video image of the scanned subject matter, while a number of axially offset channels yield image sets containing disparity information that can be employed in three-dimensional reconstruction of a surface. In other embodiments, a separate video camera and/or channel may be provided to achieve the same result, i.e., a video of an object corresponding temporally to a three-dimensional scan of the object, preferably from the same perspective, or from a perspective having a fixed, known relationship to the perspective of the camera 102. The camera 102 may also, or instead, include a stereoscopic, triscopic or other multi-camera or other configuration in which a number of cameras or optical paths are maintained in fixed relation to one another to obtain two-dimensional images of an object from a number of different perspectives. The camera 102 may include suitable processing for deriving a three-dimensional point cloud from an image set or a number of image sets, or each two-dimensional image set may be transmitted to an external processor such as contained in the computer 108 described below. In other embodiments, the camera 102 may employ structured light, laser scanning, direct ranging, or any other technology suitable for acquiring three-dimensional data, or two-dimensional data that can be resolved into three-dimensional data. While the techniques described below can usefully employ video data acquired by a video-based three-dimensional scanning system, it will be understood that any other three-dimensional scanning system may be supplemented with a video acquisition system that captures suitable video data or image data contemporaneously with, or otherwise synchronized with, the acquisition of three-dimensional data.

In one embodiment, the camera 102 is a handheld, freely-positionable probe having at least one user-input device 116, such as a button, lever, dial, thumb wheel, switch, or the like, for user control of the image capture system 100 such as starting and stopping scans. In an embodiment, the camera 102 may be shaped and sized for dental scanning More particularly, the camera may be shaped and sized for intraoral scanning and data capture, such as by insertion into a mouth of an imaging subject and passing over an intraoral surface 106 at a suitable distance to acquire surface data from teeth, gums, and so forth. The camera 102 may, through such a continuous data acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthesis, to ensure proper fitting using a previous scan of corresponding dentition, such as a tooth surface prepared for the prosthesis.

Although not shown in FIG. 1, it will be appreciated that a number of supplemental lighting systems may be usefully employed during image capture. For example, environmental illumination may be enhanced with one or more spotlights illuminating the object 104 to speed image acquisition and improve depth of field (or spatial resolution depth). The camera 102 may also, or instead, include a strobe, a flash, or some other light source to supplement illumination of the object 104 during image acquisition.

The object 104 may be any object, collection of objects, portion of an object, or other subject matter. More particularly with respect to the dental techniques discussed herein, the object 104 may include human dentition captured intraorally from a dental patient's mouth. A scan may capture a three-dimensional representation of some or all of the dentition according to a particular purpose of the scan. Thus the scan may capture a digital model of a tooth, a quadrant of teeth, or a full collection of teeth including two opposing arches, as well as soft tissue or any other relevant intraoral structures. The scan may capture multiple representations, such as a tooth surface before and after preparation for a restoration. As will be noted below, this data may be employed for subsequent modeling such as designing a restoration or determining a margin line for same. During the scan, a center channel of the camera 102 or a separate video system may capture video of the dentition from the point of view of the camera 102. In other embodiments where, for example, a completed fabrication is being virtually test fitted to a surface preparation, the scan may include a dental prosthesis such as an inlay, a crown, or any other dental prosthesis, dental hardware, dental appliance, or the like. The object 104 may also, or instead, include a dental model, such as a plaster cast, a wax-up, an impression, or a negative impression of a tooth, teeth, soft tissue, or some combination of these.

The computer 108 may include, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. In one current embodiment, the system can be operated to capture more than five thousand points per image set in real time using the techniques described herein, and store an aggregated point cloud of several million points. Of course, this point cloud may be further processed to accommodate subsequent data handling, such as by decimating the point cloud data or generating a corresponding mesh of surface data. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the object 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110. In another aspect, the display may include an autostereoscopic display or the like capable of displaying stereo images.

Communications between the computer 108 and the camera 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the camera 102 to the computer 108 may be secured. The computer 108 may generate control signals to the camera 102 which, in addition to image acquisition commands, may include conventional camera controls such as focus or zoom.

In an example of general operation of a three-dimensional image capture system 100, the camera 102 may acquire two-dimensional image sets at a video rate while the camera 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system may employ camera motion estimation to avoid the need for independent tracking of the position of the camera 102. One useful example of such a technique is described in commonly-owned U.S. application Ser. No. 11/270,135, filed on Nov. 9, 2005, the entire content of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In general, the display 110 may be operatively coupled to, and capable of receiving display signals from, the computer 108. This display may include a CRT or flat panel monitor, a three-dimensional display (such as an anaglyph display), an autostereoscopic three-dimensional display or any other suitable two-dimensional or three-dimensional rendering hardware. In some embodiments, the display may include a touch screen interface using, for example capacitive, resistive, or surface acoustic wave (also referred to as dispersive signal) touch screen technologies, or any other suitable technology for sensing physical interaction with the display 110.

The system 100 may include a computer-usable or computer-readable medium. The computer-usable medium 118 may include one or more memory chips (or other chips, such as a processor, that include memory), optical disks, magnetic disks or other magnetic media, and so forth. The computer-usable medium 118 may in various embodiments include removable memory (such as a USB device, tape drive, external hard drive, and so forth), remote storage (such as network attached storage), volatile or non-volatile computer memory, and so forth. The computer-usable medium 118 may contain computer-readable instructions for execution by the computer 108 to perform the processes described herein such as the process described in detail with reference to FIG. 6. The computer-usable medium 118 may also, or instead, store data received from the camera 102, store a three-dimensional model of the object 104, store computer code for rendering and display, and so forth.

Figure 2:
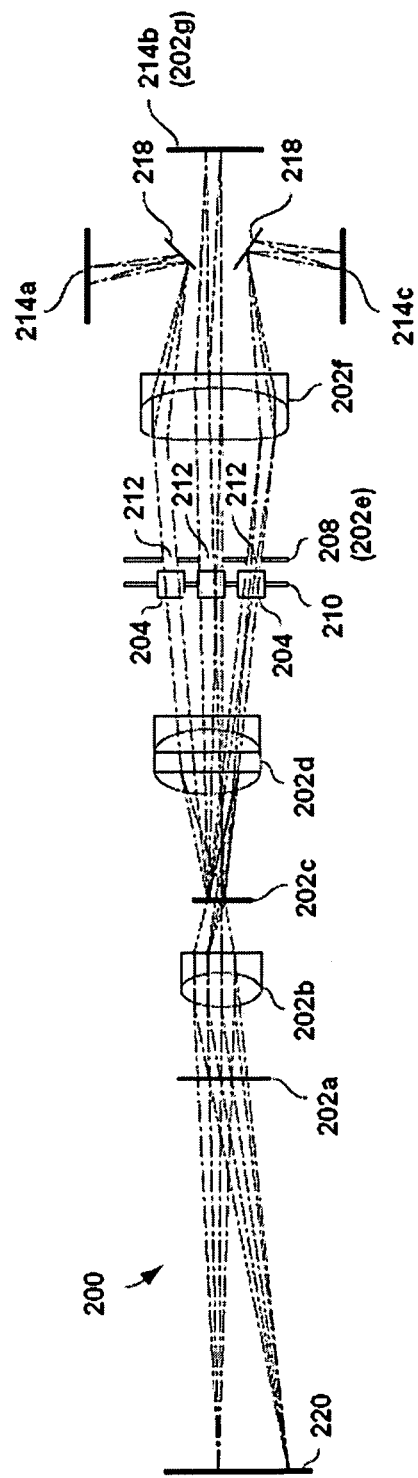
FIG. 2 depicts an optical system for a three-dimensional camera.

FIG. 2 depicts an optical system 200 for a three-dimensional camera that may be used with the systems and methods described herein, such as for the camera 102 described above with reference to FIG. 1.

The optical system 200 may include a primary optical facility 202, which may be employed in any kind of image processing system. In general, a primary optical facility refers herein to an optical system having one optical channel. Typically, this optical channel shares at least one lens, and has a shared image plane within the optical system, although in the following description, variations to this may be explicitly described or otherwise clear from the context. The optical system 200 may include a single primary lens, a group of lenses, an object lens, mirror systems (including traditional mirrors, digital mirror systems, digital light processors, or the like), confocal mirrors, and any other optical facilities suitable for use with the systems described herein. The optical system 200 may be used, for example in a stereoscopic or other multiple image camera system. Other optical facilities may include holographic optical elements or the like. In various configurations, the primary optical facility 202 may include one or more lenses, such as an object lens (or group of lenses) 202b, a field lens 202d, a relay lens 202f, and so forth. The object lens 202b may be located at or near an entrance pupil 202a of the optical system 200. The field lens 202d may be located at or near a first image plane 202c of the optical system 200. The relay lens 202f may relay bundles of light rays within the optical system 200. The optical system 200 may further include components such as aperture elements 208 with one or more apertures 212, a refocusing facility 210 with one or more refocusing elements 204, one or more sampling facilities 218, and/or a number of sensors 214a, 214b, 214c.

The optical system 200 may be designed for active wavefront sampling, which should be understood to encompass any technique used to sample a series or collection of optical data from an object 220 or objects, including optical data used to help detect two-dimensional or three-dimensional characteristics of the object 220, using optical data to detect motion, using optical data for velocimetry or object tracking, or the like. Further details of an optical system that may be employed as the optical system 200 of FIG. 2 are provided in U.S. Pat. No. 7,372,642, the entire content of which is incorporated herein by reference. More generally, it will be understood that, while FIG. 2 depicts one embodiment of an optical system 200, numerous variations are possible. One salient feature of the optical system related to the discussion below is the use of a center optical channel that captures conventional video or still images at one of the sensors 214b concurrent with one or more images from offset locations (at, e.g., 214a and 214c) that capture three-dimensional information. The center channel image may be presented in a user interface to permit inspection, marking, and other manipulation by a user during a user session as describe below.

Figure 3:
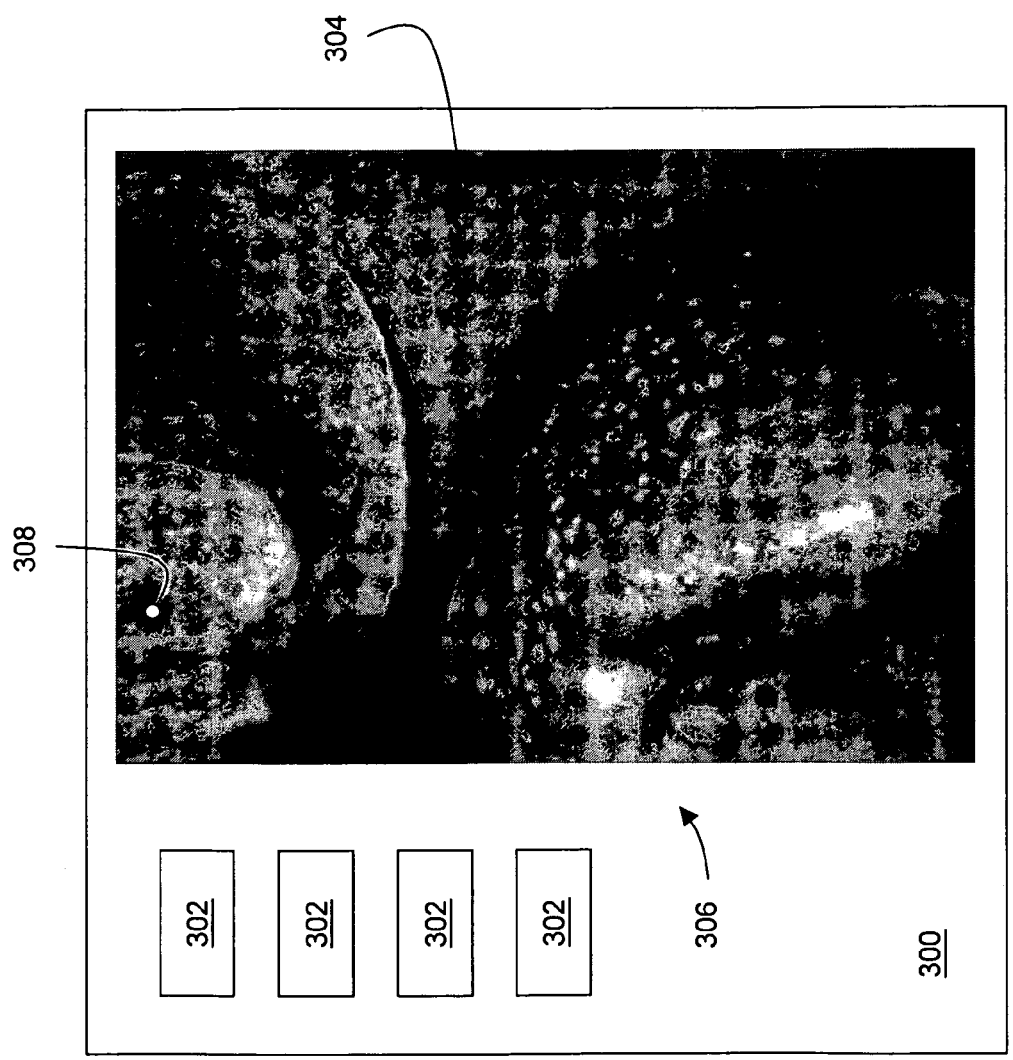
FIG. 3 depicts a user interface with an image of an object from a first viewpoint.

FIG. 3 depicts a user interface 300, which may be a graphical user interface or the like, including a number of controls 302 and a window 304 showing an image 306 captured by a three-dimensional camera such as the camera described above. FIG. 3 further depicts a user-selected location 308 on the image 306 in the window 304.

The user interface 300 may be any browser-based or application-based graphical user interface. The user interface 300 may be a two-dimensional interface rendered on a computer monitor or the like. In other embodiments, the user interface 300 may include a three-dimensional user interface rendered using anaglyph, stereoscopic, autostereoscopic, or other techniques. The controls 302 may include any suitable controls for controlling a three-dimensional camera, marking or viewing a three-dimensional model, and so forth.

The image 304 may be a frame of video or a still digital photograph, or any other color, grayscale, or other two-dimensional image captured from a camera location during a three-dimensional scan, such as a center channel image from the camera described above. As depicted here, the image 304 may depict human dentition, or a model of dentition, or other dental subject matter. However, it will be understood that the image 304 in FIG. 3 is provided for illustrative purposes, and does not limit the scope of this disclosure. The image 304 may be displayed within a window 304 or other separate area of the user interface 300.

The location 308, which may be a point or region within the window 304, may be selected using a point-and-click mouse operation, a touch screen selection, or similar user input. The location 308 within the two-dimensional display may be identified as x-y coordinates in the display. By using a three dimensional model of the object shown in the image, these x-y coordinates may be projected into the object space of the three-dimensional model and onto a surface of the model to uniquely identify a point (or region) on a surface of the three-dimensional model.

Once a surface location on the model has been identified that corresponds to the location 308 selected by the user, a catalogue of images of the object may be searched to find a best view of the surface location according to any number of useful criteria. This may include, for example, selecting an image in which the surface location is nearest to a center of the image, or selecting an image that is captured from a viewpoint substantially normal to the object surface at the surface location, or some combination of these. More generally a variety of criteria or metrics for evaluating the camera position, the quality of the image, the accuracy of three-dimensional data recovered from the viewpoint, the absence of visible defects such as specularities, the visibility of the selected point and surrounding features, and so forth, may be employed in selecting a destination image from among a set of available images that will best illustrate the selected location to a user.

Figure 4:
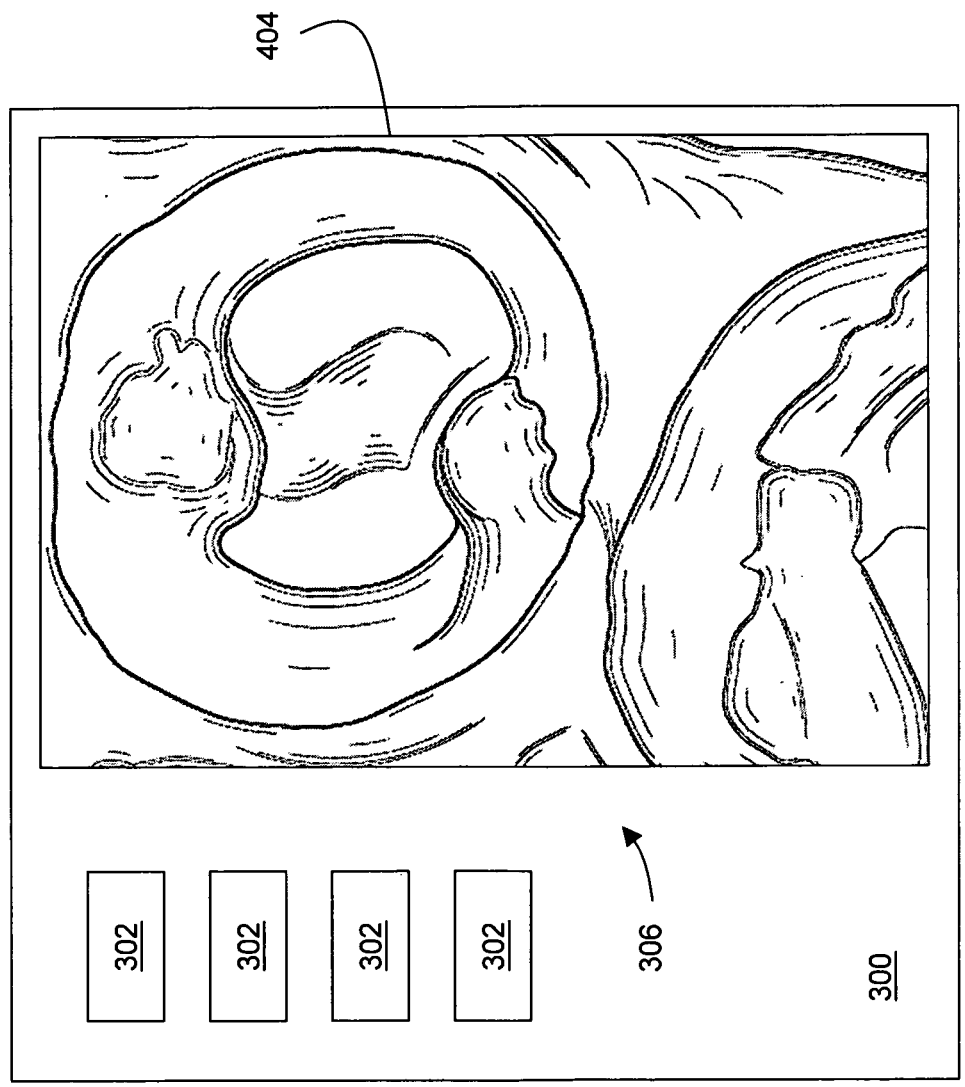
FIG. 4 depicts a user interface with a three-dimensional, model-based animation.

FIG. 4 depicts a user interface with a three-dimensional, model-based animation. In general, the user interface may be the user interface 300 described above, including identical or similar controls 302 and a window 306. However, as depicted by a line drawing in FIG. 4, the view may switch to a rendering of a three-dimensional model 404 of the subject matter of the image 304 of FIG. 3. Within the model space, a fly-over path may be determined from the viewpoint of the image 304 in FIG. 3 to the best viewpoint of the location 308, as selected from among available images using any of the techniques described above. It will be understood that the fly-over path may be determine using any number of suitable algorithms known in the art, including techniques that, e.g., maintain a substantially constant distance from the model with an orientation directed toward the surface of the model, or a straight line path from the starting point to the ending point with an orientation that tilts toward the direction of travel. Other techniques may also be employed to provide a smoother or more natural fly-over effect, such as gradual acceleration and deceleration at the ends of the path from the starting viewpoint to the ending viewpoint. As another example, one useful technique includes a zoom out at or near the beginning of a fly-over in order to provide more visual context to a user concerning location. Visualization may also be supplemented with two-dimensional or three-dimensional maps illustrating a current camera location, which may be displayed for example, in a corner of the window 306 or elsewhere in the user interface 300. Other information such as labels, landmarks, grids, or the like, may be incorporated into the animation to further aid in user orientation. Similarly, objective position and orientation information may be provided to the user during the animation, such as by using a coordinate display, a direction display, a compass, a horizon compass, and so forth.

Figure 5:
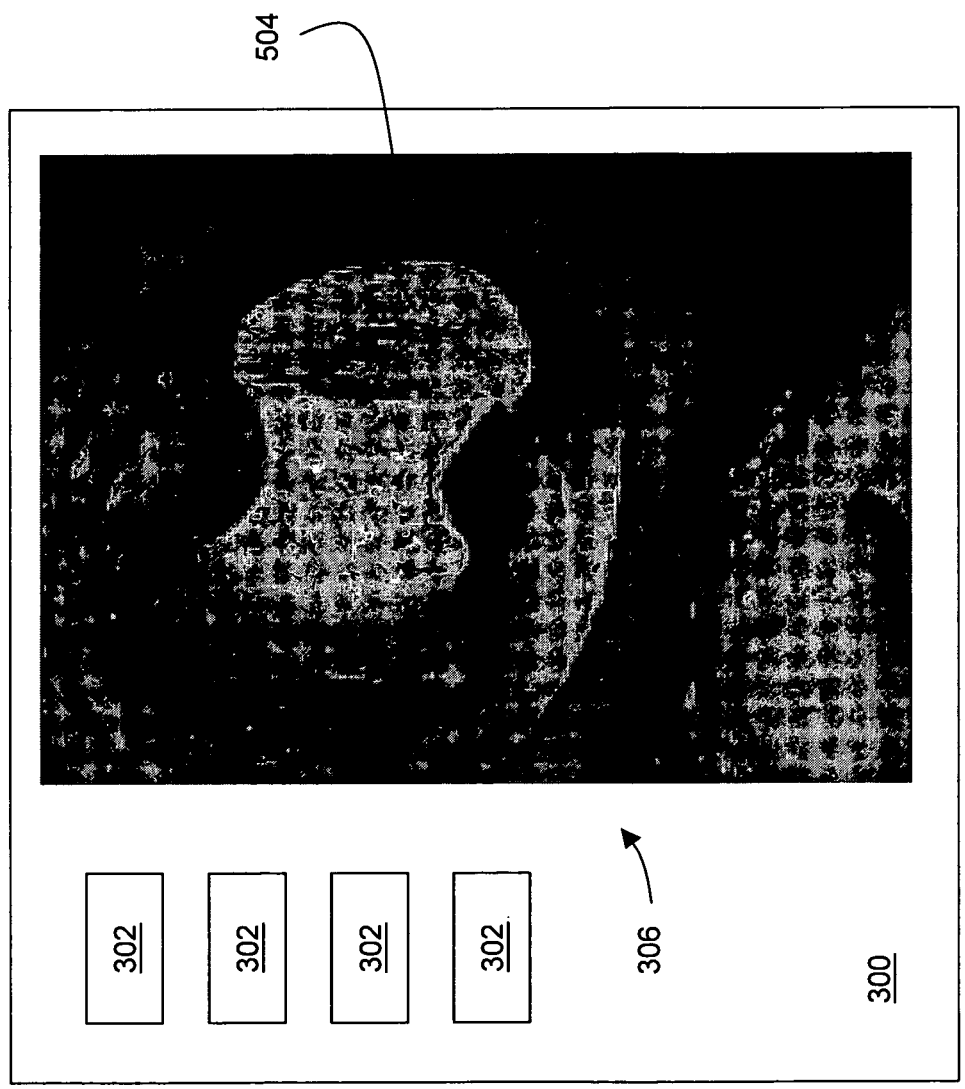
FIG. 5 depicts a user interface with an image of the object from a second viewpoint.

FIG. 5 depicts a user interface, which may be any of the graphical user interfaces described above, showing an image 504 of the subject matter from a destination viewpoint that best shows the desired location, all as generally described above. Once the destination viewpoint has been reached, the user interface 300 may revert to an image view, once again showing a photograph or other similar still image that shows the location 308 selected in FIG. 3 from an improved point of view. Thus the entire navigation may include a transition from an image view of the subject matter from a first viewpoint to a model view from that viewpoint, an animated traversal from the first viewpoint to a second viewpoint that better shows a user-selected point on a surface of the subject matter, and ending in another transition from the model view to a second image view using a second image, photograph or the like of the subject matter captured from the second viewpoint. In some embodiments, the animation may include a texture-mapped animation.

Thus in one aspect there is disclosed herein a graphical user interface for navigating among a number of images taken of an object. The graphical user interface may show a transition between images using an image-display area that alternately displays a first image captured from a first viewpoint, an animation of a spatial transition to a second viewpoint, and a second image captured from the second viewpoint. In some embodiments the first image and the second image may be video data that originates from a center channel of a multi-aperture camera having a center channel and two side channels that capture images used for the creation of a three-dimensional model of scanned subject matter. For example and without limitation, the camera may include the three-dimensional camera 102 of FIG. 1. In some embodiments, the object that is scanned may include human dentition such as teeth, gums, dentures, braces, or the like, as well as prepared tooth surfaces, dental models, and other dental subject matter.

Figure 6:
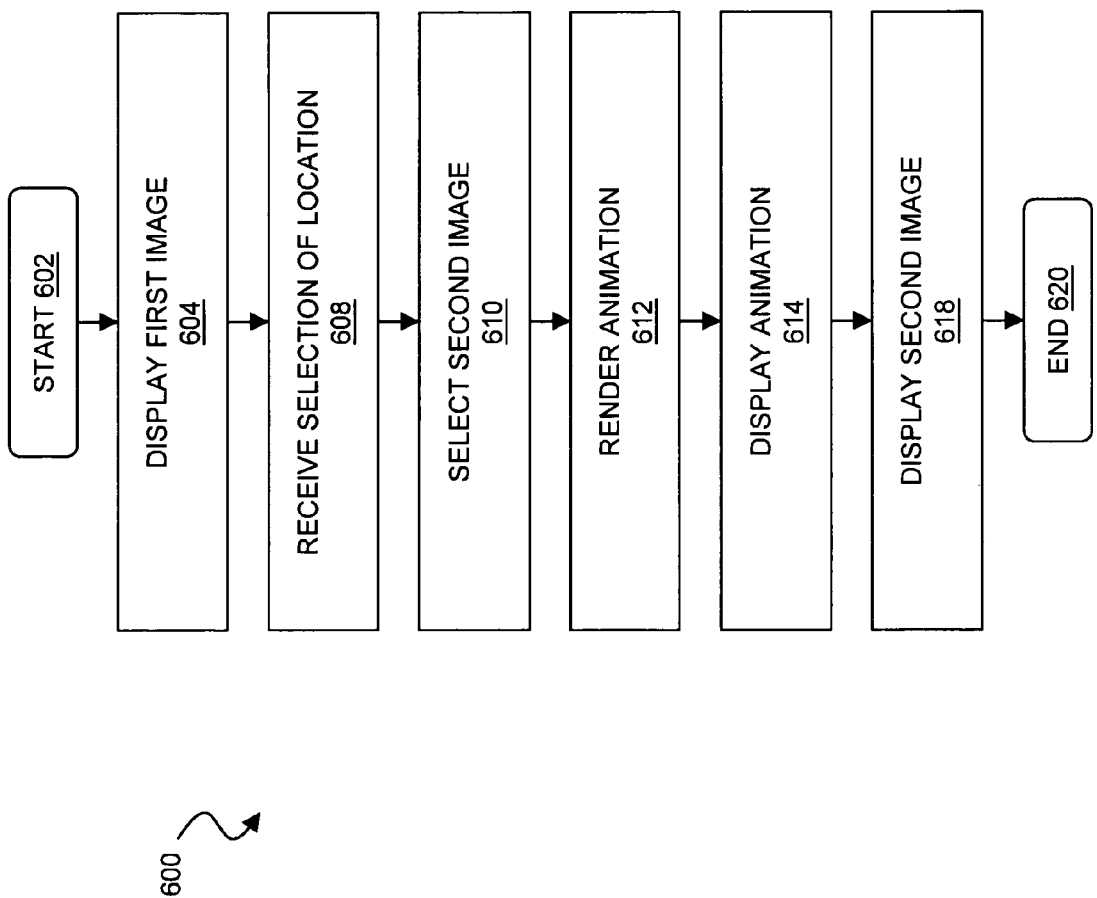
FIG. 6 depicts a process for navigating among a number of images.

FIG. 6 depicts a process for navigating among a number of images. The process 600 may begin 602 with displaying a first image as shown in step 604. The image may be any of the images described above including a still image, a video frame, or any other digital or similar visual image of an object. The first image may be selected from a number of images taken of the object. In general, the first image may depict a visually discernable surface of the object. For example and without limitation, the first image may be one of a number of video frames that show a surface of a tooth or other dentition. In some embodiments, the images may include frames of video data that originate from a multi-aperture camera that uses a center channel to capture undistorted images of an object and one or more side channels that capture distorted images with spatial information used to reconstruct a three-dimensional model of the object such as the camera described above with reference to FIG. 1.

As shown in step 608, a user selection of a location on the surface of the object may be received. In embodiments, the selection may correspond to a user action using the image as displayed. For example, a user may view the first image in a graphical user interface and then use a mouse to affect and point-and-click operation with a cursor within the graphical user interface, or the user may view the first image in an interface that includes a touch screen and touch the display at a desired location on the surface of the object. It will be understood that numerous additional input devices are known such as a touch screen stylus or other pointer, or a joystick, a thumbwheel, or a manual cursor movement using arrows or other keys on a keyboard or the like, and any such input device(s) may be adapted for use alone or in combination to receive a user selection of a location on an image displayed within a user interface. It will be understood that while the location may be a specific x-y location within the user interface, or a corresponding point on the surface of the object, a location may more generally be any region or area around and/or including the user selected point, either within the field of view or on the surface of an object within the field of view.

As shown in step 610, a second image may be selected. In general, the second image is selected from a number of images of an object, such as a sequence of images captured along a camera path traversed during a three-dimensional scan of the object. The selected image may, for example, provide a second viewpoint of the object that offers an improved perspective on the user-selected location on the surface of the object. The improved perspective may be evaluated, for example, using any of the techniques described above (e.g., viewpoint normal to surface, location centered within image, or some combination of these). In general, a three-dimensional camera may capture a finite number of images from a finite number of viewpoints during a scan, and in certain embodiments, a substantial number of these images may be discarded during or after processing for three-dimensional reconstruction (such as to conserve storage or processing resources). Thus it will be understood that an improved perspective, view, or viewpoint as described herein generally refers to a best fit from among a finite collection of images rather than an ideal image responsive to the criteria employed. Additionally, some embodiments may display a plurality of candidate images selected from the number of images taken of the object. This may be helpful, for example, where none of the available images correspond to a viewpoint tightly coupled to the selection criteria, or where a number of images provide useful but somewhat different perspectives on the selected location. In such embodiments, the act of selecting the second image may include receiving a selection by the user of one of the plurality of candidate images as the second image of the object.

As shown in step 612, once a second viewpoint is selected an animation may be rendered that represents a spatial transition from the first viewpoint to the second viewpoint. This may, for example, be a substantially smooth and continuous animation rendered using a three-dimensional model of the object. In embodiments, the three-dimensional model may include a point cloud, a polygonal surface model or any other point, surface, or volume representation of the object in three-dimensional space. In some embodiments, the model may include a texture map that is derived from at least one image of the number of images described above. This texture-mapped model may better preserve a natural visual appearance of the object during the spatial transition from the first viewpoint to the second viewpoint. It will be understood that the spatial transition may be animated as a fly-over using any of the techniques described above to help maintain a user's spatial orientation with respect to the subject matter during the transition between viewpoints. In general, the spatial transition from the first viewpoint to the second viewpoint includes a translation and a rotation which may be achieved using any of a variety of simulated camera paths, any of which may be animated using the three-dimensional model.

As shown in step 614, the animation may be displayed, such as in a two-dimensional or three-dimensional interface. It will be appreciated that while rendering of animation of a spatial transition is described separately from display of the spatial transition, these steps may be performed concurrently such as where each frame of display output is generated as each image of the rendered animation becomes available, or where animation results are calculated directly in a display buffer. All such variations are intended to fall within the scope of this disclosure. After the spatial transition is rendered and/or displayed for a user, the second image may be displayed as shown in step 618, and the process 600 may end 620.

The elements depicted in flow charts and block diagrams throughout the figures imply logical boundaries between the elements. However, it will be understood that the depicted elements and the functions thereof may be implemented as parts of a monolithic software structure, as standalone software modules, or as modules that employ external routines, code, services, and so forth, or any combination of these, and all such implementations are within the scope of the present disclosure. Thus, while the foregoing drawings and description set forth functional aspects of the disclosed systems, no particular arrangement of software for implementing these functional aspects should be inferred from these descriptions unless explicitly stated or otherwise clear from the context.

Similarly, it will be appreciated that the various steps identified and described above may be varied, and that the order of steps may be adapted to particular applications of the techniques disclosed herein. For example, the user interface may provide a user interrupt to pause or terminate the fly-over with any number of exit conditions such as a jump to a nearest image from the number of images, or manual control of navigation in the model view. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods or processes described above, and steps thereof, may be realized in hardware, software, or any combination of these suitable for a particular application. The hardware may include a general-purpose computer and/or dedicated computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method of navigating among a number of two-dimensional digital images taken of an object by a camera, the method comprising:
    displaying a first image of the object from the camera, the first image selected from the number of images and showing a surface of the object from a first viewpoint; and
    in response to receiving a selection of an image location within the first image, automatically performing the steps of:
        determining a location on the surface of the object based on the selection of the image location;
        selecting a second image of the object from the number of images taken of the object, the second image selected to provide an improved view of the location on the surface of the object from a second viewpoint, wherein the improved view is more normal to the surface of the object at the location than the first image;
        transitioning from a first image view of the first image from the first viewpoint to a model view of a three-dimensional model of the object representing the object in three-dimensional space, wherein the three-dimensional model comprises a three-dimensional set of points forming a three-dimensional view of the object reconstructed from the number of images;
        displaying an animation from the first viewpoint to the second viewpoint in the model view using the three-dimensional model, wherein the animation comprises displaying a spatial transition of the three-dimensional model from the first viewpoint to the second viewpoint;
        transitioning from the model view to a second image view of the second image from the second viewpoint; and
        displaying the second image,
        except that if a user interrupt of the animation is received during display of the animation, then exiting the animation at a point of the interrupt in the model view with an automatic jump to a nearest image from the number of images at the point of the interrupt and displaying the nearest image in another image view.

2. The method of claim 1 wherein receiving the selection of the location includes receiving the selection from within a graphical user interface.

3. The method of claim 2 wherein receiving the selection includes an input from a cursor control tool.

4. The method of claim 1 wherein selecting the second image includes displaying a plurality of candidate images selected from the number of images taken of the object and receiving a user selection of one of the plurality of candidate images.

5. The method of claim 1 wherein the number of images includes a plurality of frames of video data that originate from a center channel of a video camera having one or more side channels that capture data used to generate the three-dimensional model.

6. The method of claim 1 wherein selecting the second image includes selecting a one of the number of images having the location nearest to a center thereof.

7. The method of claim 1 wherein the object includes human dentition.

8. The method of claim 7 wherein the object includes at least one of teeth, gums, dentures, and braces.

9. The method of claim 7 wherein the object includes a prepared tooth surface.

10. The method of claim 1 wherein the determining the location comprises projecting two-dimensional coordinates of the image location onto a surface of the three-dimension model to identify the location on the surface of the object.

11. The method of claim 1 wherein the displaying the animation comprises displaying a rotation of the three-dimensional model from the first viewpoint to the second viewpoint.

12. A system for navigating among a number of two-dimensional digital images taken of an object by a camera, the system comprising:
a computer;
a display operatively coupled to the computer;
a user input device that receives a user selection, the user input device operatively coupled to the computer; and
a computer-usable medium operatively coupled to the computer, the computer-usable medium having stored within it computer-readable instructions for execution by the computer to perform a method comprising the steps of:
displaying a first image of the object from the camera, the first image selected from the number of images and showing a surface of the object from a first viewpoint; and
in response to receiving a selection of an image location within the first image, automatically performing the steps of:
determining a location on the surface of the object based on the selection of the image location;
selecting a second image of the object from the number of images taken of the object, the second image selected to provide an improved view of the location on the surface of the object from a second viewpoint, wherein the improved view is more normal to the surface of the object at the location than the first image;
transitioning from a first image view of the first image from the first viewpoint to a model view of a three-dimensional model of the object representing the surface of the object in three-dimensional space, wherein the three-dimensional model comprises a three-dimensional set of points forming a three-dimensional view of the object reconstructed from the number of images;
displaying an animation from the first viewpoint to the second viewpoint in the model view using the three-dimensional model, wherein the animation comprises displaying a spatial transition of the three-dimensional model from the first viewpoint to the second viewpoint;
transitioning from the model view to a second image view of the second image from the second viewpoint; and
displaying the second image,
except that if a user interrupt of the animation is received during display of the animation, then exiting the animation at a point of the interrupt in the model view with an automatic jump to a nearest image from the number of images at the point of the interrupt and displaying the nearest image in another image view.

13. The system of claim 12 wherein the user input device includes a cursor control tool.

14. The system of claim 12 further comprising:
a three-dimensional camera having a left channel and a right channel that capture spatial information, the camera operatively coupled to the computer; and
computer-readable instructions for execution by the computer to construct the three-dimensional model from the spatial information, the computer-readable instructions stored within the computer-usable medium.

15. The system of claim 12 wherein the computer-usable medium includes one or more of a computer chip, an optical disk, and a magnetic disk.

16. The system of claim 12 wherein the display includes a three-dimensional display.

17. The system of claim 16 wherein the display includes an autostereoscopic display.

18. The system of claim 16 wherein receiving the selection of the location includes receiving the selection from within a graphical user interface.

19. The system of claim 16 wherein selecting the second image includes displaying a plurality of candidate images selected from the number of images taken of the object and receiving a user selection of one of the plurality of candidate images.

20. The system of claim 16 wherein selecting the second image includes selecting a one of the number of images having the location nearest to a center thereof.

21. The system of claim 12 wherein the determining the location comprises projecting two-dimensional coordinates of the image location onto a surface of the three-dimension model to identify the location on the surface of the object.

22. The system of claim 12 wherein the displaying the animation comprises displaying a rotation of the three-dimensional model from the first viewpoint to the second viewpoint.

* * * * *